United States Patent [19]

Daum et al.

[11] Patent Number: 4,871,864
[45] Date of Patent: Oct. 3, 1989

[54] CARBAMOYLOXYTHIOPHENE FUNGICIDES

[75] Inventors: Werner Daum, Krefeld; Gerd Hänssler, Leverkusen; Pieter Ooms, Krefeld, all of Fed. Rep. of Germany

[73] Assignee: Bayer Aktiengesellschaft, Leverkusen, Fed. Rep. of Germany

[21] Appl. No.: 310,405

[22] Filed: Feb. 13, 1989

Related U.S. Application Data

[62] Division of Ser. No. 165,685, Mar. 9, 1988, Pat. No. 4,839,381, which is a division of Ser. No. 37,918, Apr. 13, 1987, Pat. No. 4,757,085.

[30] Foreign Application Priority Data

Apr. 24, 1986 [DE] Fed. Rep. of Germany ....... 3613792

[51] Int. Cl.$^4$ ............................................. C07D 409/00
[52] U.S. Cl. ....................................................... 549/60
[58] Field of Search ........................................... 549/60

[56] References Cited

U.S. PATENT DOCUMENTS 4,767,757  8/1988  Daum et al. ........................... 549/60

FOREIGN PATENT DOCUMENTS 0032748   7/1981   European Pat. Off. .
0093384  11/1983   European Pat. Off. .
1020641  12/1957   Fed. Rep. of Germany .
1913273   9/1970   Fed. Rep. of Germany .
3402625   8/1985   Fed. Rep. of Germany .

OTHER PUBLICATIONS

10th International Congress of Plant Protection 1983, vol. 1 pp. 400–407.
Justus Liebigs Annalen Der Chemie, vol. 562, (1949), pp. 75–136.

*Primary Examiner*—Alan Siegel

*Attorney, Agent, or Firm*—Sprung Horn Kramer & Woods

[57]    ABSTRACT

Fungicidally active carbamoyloxythiophene derivatives of the formula

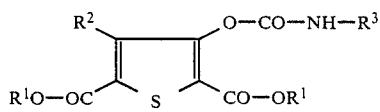

in which
  $R^1$ represents alkyl, alkoxyalkyl, alkylthioalkyl fluoroalkyl, cyanoalkyl, alkenyl, alkynyl, or cycloalkyl,
  $R^2$ represents alkyl, optionally substituted furyl or optionally substituted phenyl,
  $R^3$ represents aliphatic or carbocyclic cyanoalkyl, the

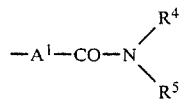

radical or the —$A^2$-CO-OR$^6$ radical,
  where
  $A^1$ represents an alkylene radical,
  $A^2$ represents an alkylene radical or denotes a direct bond,
  $R^4$ and $R^5$, independently of one another, represent alkyl, or
  $R^4$ and $R^5$, together with the nitrogen atom which they neighbor, form a heterocyclic ring which may contain further hetero atoms and is optionally substituted, and
  $R^6$ represents alkyl,
and novel intermediates therefor.

1 Claim, No Drawings

CARBAMOYLOXYTHIOPHENE FUNGICIDES

This is a division, of application Ser. No. 165,685, filed Mar. 9, 1988, now U.S. Pat. No. 4,839,381, which is a division of Ser. No. 037,918 filed Apr. 13, 1987 now U.S. Pat. No. 4,757,085 issued July 12, 1988.

The present invention relates to new carbamoyloxythiophene derivatives, processes for their preparation, and their use as pesticides, above all as fungicides.

It is already known that thiophene derivatives such as, for example, 2,5-bis-(butoxycarbonyl)-3-methyl-4-styrylcarbonyloxythiophene and 2,5-bis-(ethoxycarbonyl)-3,4-bis-(benzoyloxy)-thiophene, have fungicidal properties.

2,5-bis-(isopropoxycarbonyl)-3-methyl-4-(3-methyl-4-(3-methylbenzoyloxy)-thiophene, which is known from T. Wada et al., Proceedings of the 10th Internat. Congress of Plant Protection, Nov. 20–25., 1983, Brighton, Vol. 1 pages 400–407, should particularly be mentioned. The action of these compounds may not always be completely satisfactory under certain conditions, such as, for example, at low applicational amounts and concentrations.

New carbamoyloxythiophene derivatives of the general formula (I)

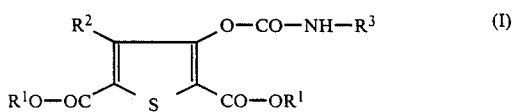
(I)

in which
R$^1$ represents alkyl, alkoxalkyl, alkylthioalkyl, fluoroalkyl, cyanoalkyl, alkenyl, alkynyl, or cycloalkyl,
R$^2$ represents alkyl, optionally substituted furyl or optionally substituted phenyl,
R$^3$ represents aliphatic or carbocyclic cyanoalkyl, the

radical or the —A$^2$—CO—OR$^6$ radical, where
A$^1$ represents an alkylene radical,
A$^2$ represents an alkylene radical or denotes a direct bond,
R$^4$ and R$^5$, independently of one another, represent alkyl, or
R$^4$ and R$^5$, together with the nitrogen atom which they neighbor form a heterocyclic ring which may contain further hetero atoms and is optionally substituted, and
R$^6$ represents alkyl,
have been found.

It has furthermore been found that the new carbamoyloxythiophene derivatives of the general formula (I)

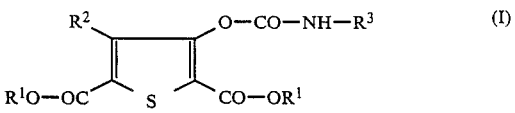
(I)

in which
R$^1$ represents alkyl, alkoxyalkyl, alkylthioalkyl, fluoroalkyl, cyanoalkyl, alkenyl, alkynyl or cycloalkyl,
R$^2$ represents alkyl, optionally substituted furyl or optionally substituted phenyl,
R$^3$ represents aliphatic or carbocyclic cyanoalkyl, the

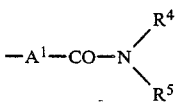

radical or the —A$^2$—CO—OR$^6$ radical, where
A$^1$ represents an alkylene radical,
A$^2$ represents an alkylene radical or denotes a direct bond,
R$^4$ and R$^5$, independently of one another, represent alkyl, or
R$^4$ and R$^5$, together with the nitrogen atom which they neighbor form a heterocyclic ring which may contain further hetero atoms and is optionally substituted, and
R$^6$ represents alkyl,
are obtained when either
(a) an isocyanate of the general formula (II)

$$OCN-R^3 \qquad (II)$$

in which
R$^3$ has the above-mentioned meaning, is reacted wit hydroxythiphene derivatives of the general formula (III)

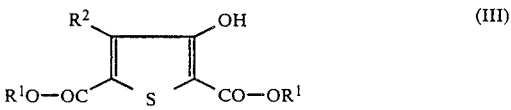
(III)

in which
R$^1$ and R$^2$ have the above-mentioned meanings, if appropriate in the presence of a solvent or diluent and if appropriate in the presence of a catalytically active substance, or when
(b) a 4-hydroxythiophene derivative of the formula (III) is reacted, in a first stage, with phosgene in the presence of a hydrochloric acid-binding agent to form a 4-chlorocarbonyloxythiophene derivative of the formula (IV)

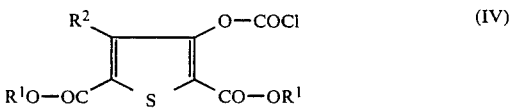
(IV)

and then, in a second stage, the 4-chlorocarbonyloxythiophene derivative of the formula (IV) is reacted with an amine of the formula (V)

$$NH_2-R^3 \qquad (V)$$

or with a salt corresponding to the formula (V), in the presence of an acid-binding agent.

It has furthermore been found that the new carbamoyloxythiophene derivatives of the formula (I) have biological properties.

Surprisingly, the carbamoyloxythiophene derivatives of the formula (I) according to the invention display an activity against a very wide variety of pests which is superior to that of the compounds, known from the state of the art, of the same type of action or compared to structurally similar compounds.

The carbamoyloxythiophene derivatives according to the invention are generally defined by the formula (I). Preferred compounds of the formula (I) are those in which $R^1$ represents straight-chain or branched alkyl having 1 to 6 carbon atoms, alkoxyalkyl or alkylthioalkyl each having 1 to 5 carbon atoms in each straight-chain or branched alkyl part, fluoroalkyl having 1 to 4 carbon atoms and 1 to 9 fluorine atoms, straight-chain or branched cyanoalkyl having 1 to 6 carbon atoms in the alkyl part, straight-chain or branched alkenyl having 2 to 5 carbon atoms, straight-chain or branched alkynyl having 3 to 6 carbon atoms, or cycloalkyl having 5 to 7 carbon atoms, $R^2$ represents straight-chain or branched alkyl having 1 to 5 carbon atoms, furyl, benzofuryl or benzofuryl which is mono- or disubstituted by halogen, alkyl or alkoxy, or phenyl which is optionally mono- to pentasubstituted, identically or differently, by alkyl having 1 to 4 carbon atoms, by alkoxy or alkylthio each having 1 to 4 carbon atoms, by halogen, by nitro, or by halogenoalkyl, halogenoalkoxy or halogenoalkylthio each having 1 to 4 carbon atoms and each having 1 to 5 identical or different halogen atoms, halogen, as such, or in the radicals such as halogenoalkyl, representing fluorine, chlorine, bromine or iodine, preferably fluorine or chlorine, $R^3$ represents straight-chain or branched or saturated, cyclic cyanoalkyl having 1 to 6 carbon atoms in the alkyl part a

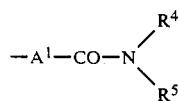

radical or the $-A^2-CO-OR^6$ radical, where
  $A^1$ represents alkylene having 1 to 6 carbon atoms,
  $R^4$ and $R^5$, independently of one another, represent alkyl having 1 to 5 carbon atoms, or
  $R^4$ and $R^5$, together with the nitrogen atom which they neighbor may form a saturated or unsaturated, heterocyclic ring having up to 6 carbon atoms, which may be interrupted by further oxygen atoms and which may be mono- to pentasubstituted, identically or differently, by alkyl having 1 to 4 carbon atoms,
  $A^2$ represents alkylene having 1 to 6 carbon atoms or denotes a direct bond, and
  $R^6$ represents alkyl having 1 to 10 carbon atoms.

Particularly preferred compounds of the formula (I) are those in which $R^1$ represents straight-chain or branched alkyl having 1 to 5 carbon atoms, alkoxyalkyl or alkylthioalkyl each having 1 to 4 carbon atoms in each straight-chain or branched alkyl part, fluoroalkyl having 1 or 2 carbon atoms and 1 to 5 fluorine atoms, straight-chain or branched cyanoalkyl having 1 to 5 carbon atoms in the alkyl part, straight-chain or branched alkenyl having 2 to 4 carbon atoms, straight-chain or branched alkynyl having 3 to 5 carbon atoms, or cycloalkyl having 5 or 6 carbon atoms, $R^2$ represents straight-chain or branched alkyl having 1 to 4 carbon atoms, furyl, or phenyl which is optionally mono- to trisubstituted, identically or differently, by alkyl having 1 to 3 carbon atoms, by alkoxy or alkylthio each having 1 to 3 carbon atoms, by fluorine, by chlorine, by nitro, or by halogeno alkyl, halogenoalkoxy or halogenoalkylthio each having 1 or 2 carbon atoms and each having 1 to 5 identical or different halogen atoms, halogen representing fluorine or chlorine in the radicals such as halogenoalkyl, $R^3$ represents straight-chain or branched or saturated, cyclic cyanoalkyl having 1 to 6 carbon atoms in the alkyl part, a

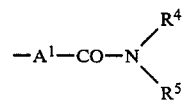

radical or the $-A^2-CO-OR^6$ radical, where
  $A^1$ represents alkylene having 1 to 5 carbon atoms,
  $R^4$ and $R^5$, independently of one another, represent alkyl having 1 to 3 carbon atoms, or
  $R^4$ and $R^5$, together with the nitrogen atom which they neighbor may form a saturated or unsaturated, heterocyclic ring, having up to 6 carbon atoms, which may be interrupted by a further oxygen atom and which may optionally be mono- to trisubstituted, identically or differently, by methyl or ethyl,
  $A^2$ represents alkylene having 1 to 5 carbon atoms or denotes a direct bond, and
  $R^6$ represents alkyl having 1 to 8 carbon atoms.

Compounds of the formula (I) which may particularly be mentioned are those in which $R^1$ represents methyl, ethyl, n- or iso-propyl, 2,2-dimethylpropyl, 2-methoxyethyl, 2-ethoxyethyl, methoxypropyl, 2-methylthioethyl, 2-ethylthioethyl, 2,2,2-trifluoroethyl, cyanomethyl, 2-cyanoethyl, allyl, methallyl, 3-propinyl, 1,1-dimethyl-3-propinyl or cyclopentyl, $R^2$ represents methyl, ethyl, n-propyl, isopropyl, n-butyl, sec.-butyl, iso-butyl, tert.-butyl, furyl, phenyl or phenyl which is mono- to trisubstituted, identically or differently, by methyl, ethyl, fluorine an chlorine, $R^3$ represents straight-chain or branched cyanoalkyl having 2 to 6 carbon atoms in the alkyl part, saturated cyclic cyanoalkyl having 5 or 6 carbon atoms in the ring, the

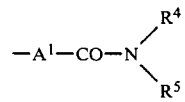

radical or the $-A^2-CO-OR^6$ radical, where
  $A^1$ represents alkylene having 1 to 5 carbon atoms,
  $R^4$ and $R^5$, independently of one another, represent methyl or ethyl, or
  $R^4$ and $R^5$, together with the nitrogen atom which they neighbour, form a 6-membered ring which may be interrupted by an oxygen atom and which may optionally be mono- to trisubstituted, identically or differently, by methyl or ethyl, A² represents alkylene having 1 to 5 carbon atoms or denotes a direct bond, and R⁶ represents alkyl having 1 to 8 carbon atoms.

Compounds of the formula (I) which should particularly be emphasized are those in which R¹ represents methyl, ethyl, isopropyl, n-propyl, sec.-butyl, 2,2-dimethylpropyl or cyclopentyl, R² represents methyl, isopropyl, furyl or phenyl, R³ represents 1-cyano-1-methylethyl, 2-cyanoethyl, 5-cyanopentyl or the —A²-COOR⁶ radical, where A² denotes a direct bond or a pentylene radical, and R⁶ denotes methyl, ethyl, isopropyl, butyl, 2,2-dimethylpropyl, 2-methylhexyl or octyl.

If, for example, 2,5-bis-(ethoxycarbonyl)-3-phenyl-4-hydroxythiophene and 1-cyano-1-methylpropyl isocyanate are used as starting matrials and triethylenediamine is used as catalyst for the preparation of the compounds of the formula (I) according to the invention by process (a), the course of the reaction can be represented by the following equation:

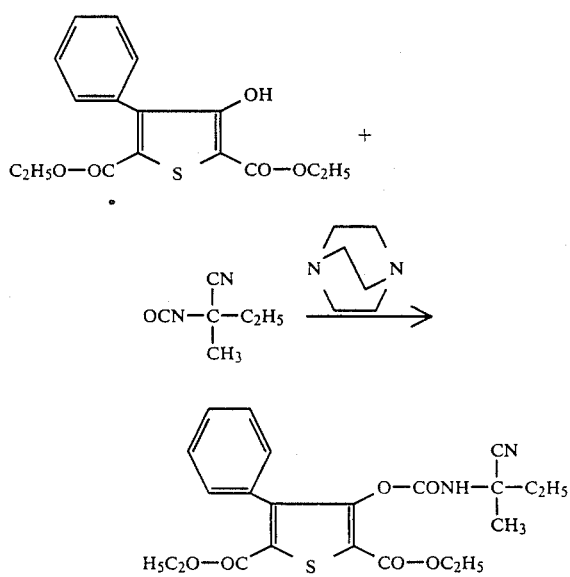

If 2,5-bis-(n-propoxycarbonyl)-3-methyl-4-chlorocarbonyloxy-thiophene and 1-cyano-1-amino-cyclohexane are used as starting materials for the preparation of the compounds of the formula (I) according to the invention by process (b), the course of the reaction can be represented by the following equation:

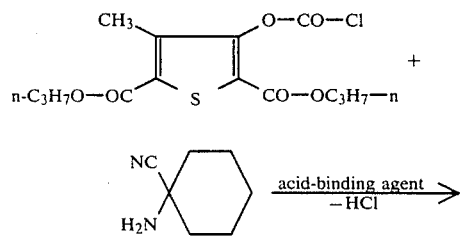

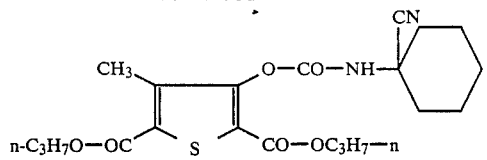

The isocyanates required as starting materials for carrying out the process (a) according to the invention are generally defined by the formula (II). Most of the compounds are known and can be prepared by known methods. The isocyanates can be prepared, for example, by reacting the amino compounds with phosgene (cf., for example, Liebigs Ann. Chem. 562, 75–136 (1949)), by reacting chlorocarbonyl isocyanate with alcohols or with amines (cf. DOS (German Published Specification) 1,913,273), or by thermal cleavage of the phenoxycarbonylamino compounds.

The following should particularly be mentioned here: 2-cyanoethyl isocyanate, 1-cyano-1-methylethyl isocyanate, 1-cyano-1-methyl-propyl isocyanate, 1-cyano-1-ethyl-propyl isocyanate, 1-cyano-cyclopent-1-yl isocyanate, 1-cyanocyclohex-1-yl isocyanate, 3-cyanopropyl isocyanate, 5-cyanopentyl isocyanate, 6-cyanohexyl isocyanate, N-morpholinocarbonylmethyl isocyanate, 1-(N,N-diethylaminocarbonyl)-ethyl isocyanate, N-pyrrolidinocarbonylethyl isocyanate, N-piperidino-carbonyl-propyl isocyanate, N,N-dimethylaminocarbonylpentyl isocyanate, methoxycarbonylmethyl isocyanate, ethoxycarbonylmethyl isocyanate, butoxycarbonylethyl isocyanate, isobutoxycarbonylethyl isocyanate, 1-methoxycarbonyl-1-methylethyl isocyanate, 1-propoxycarbonyl-1-methyl-ethyl isocyanate, 1-ethoxycarbonyl-1-ethyl-ethyl isocyanate, 1-isobutoxycarbonyl-1-ethyl-ethyl isocyanate, methoxycarbonyl-propyl isocyanate, methoxycarbonyl-pentyl isocyanate, isopropoxycarbonyl-pentyl isocyanate sec.-butyloxycarbonyl-pentyl isocyanate allyloxycarbonylpentyl-isocyanate, propargyloxycarbonyl-pentyl isocyanate, 2-ethoxycarbonyl-2-ethyl-butyl isocyanate, butoxycarbonylpentyl isocyanate, 2,2-dimethylproploxycarbonylpentyl isocyanate, methoxycarbonyl isocyanate, ethoxycarbonyl isocyanate, 2,2-dimethylpropyloxycarbonyl isocyanate, 2-ethylhexyloxycarbonyl isocyanate and octyloxycarbonyl isocyanate.

Furthermore, 3-hydroxythiophene derivatives which are generally defined by the formula (III) are required for the reaction according to process (a) to form the compounds according to the invention. Some of the starting compounds of the formula (III) are known, but can be prepared by generally known processes, such as, for example, from thiodiacetates and 2-oxocarboxylates under alkaline conditions, for example under the action of potassium tert.-butanolate, and, after the condensation, treatment with an acid (cf. European Patent Specification 93,384 and DAS (German Published Specification) 1,020,641). The reaction can be illustrated by the following equation:

$$R^2-CO-CO-OR +$$ (III)

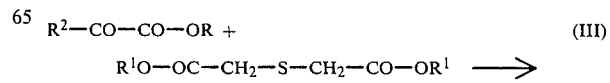

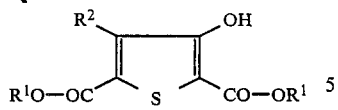

$R^1$ and $R^2$ have the above-mentioned meanings.

The following should be mentioned individually: methyl, ethyl, isopropyl, 2,2-dimethylpropyl, cyanomethyl, 2-cyanoethyl, 1-cyano-1-methylethyl, 2,2,2-trifluoroethyl, 2-methoxyethyl, 2-butylthioethyl, 2-ethylthioethyl, allyl, methylallyl, propargyl and 1,1-dimethylpropargyl 3-methyl-4-hydroxythiophene-2,5-dicarboxylate; 2,2,2-trifluoroethyl 3-ethyl-, 3-propyl-, 3-isopropyl-, 3-butyl- and 3-tert.-butyl-4-hydroxy-thiophene-2,5-dicarboxylate; methyl 3-(fur-3-yl)-4-hydroxythiophene-2,5-dicarboxylate; and cyclopentyl 3-phenyl-, 3-(4-chlorophenyl)-4-hydroxy-thiophene-2,5-dicarboxylate.

Those compounds of the formula III in which $R^2$ is an optionally substituted furyl radical are hitherto unknown. They are compounds of the general formula

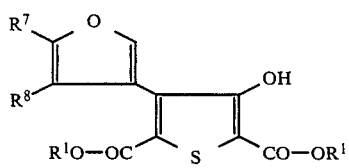

in which $R^1$ has the above-mentioned meaning and $R^7$ and $R^8$ denote hydrogen, or, together with the furyl radical to which they are bound, represent a benzofuryl radical of the formula (VII)

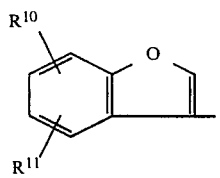

in which $R^{10}$ and $R^{11}$, independently of one another, may denote hydrogen, halogen, alkyl or alkoxy.

The compounds of the formula (IIIa) are obtained by reacting a thiodiacetate with a 2-(fur-3-yl)-2-oxo-acetate in the presence of potassium tert.-butanolate, and subsequently pouring into acid.

The 2-(fur-3-yl)-2-oxo-acetates of the general formula (VIII)

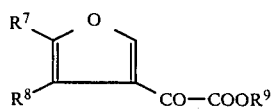

in which $R^7$ and $R^8$ have the above-mentioned meanings and $R^9$ represents alkyl which is optionally substituted by halogen or alkoxy, Likewise new, which are employed for this are obtained when fur-3-yl-glycolates of the general formula (VI)

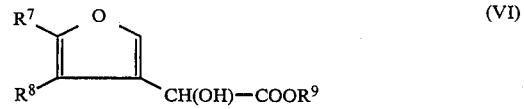

in which $R^7$, $R^8$ and $R^9$ have the above-mentioned meanings, are reacted with oxidants in an inert organic solvent.

Particularly suitable compounds of the formula (VI) are those in which $R^7$ and $R^8$ represent hydrogen or, together with the furyl radical to which they are bound, represent a benzofuryl radical of the formula VII, in which $R^{10}$ and $R^{11}$, independently of one another, denote hydrogen or methoxy, and $R^9$ represents n-butyl.

If, for example, trifluoroethyl fur-3-ylglycolate and chromium trioxide are used as starting materials for the preparation of the compounds of the formula (VIII), the course of the reaction can be represented by the following equation:

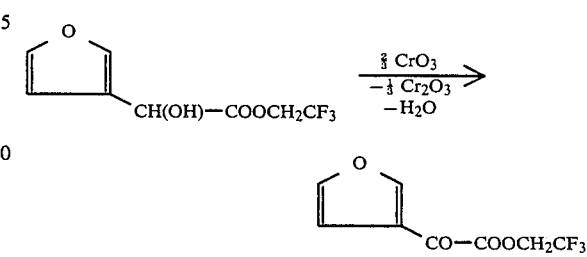

Some of the fur-3-yl-glycolates, generally defined by the formula (VI), which are required as starting materials for carrying out the process are known (J. Org. Chem. 42, 1089 (1977)). They are obtained when glyoxylates are added photochemically to furans and the 2,7-dioxabicyclo[3.2.0]hept-3-enes are subsequently isomerized using acid.

Mention should be made here of methyl, ethyl, propyl, isopropyl, butyl, sec.-butyl, isobutyl, n-amyl, trifluoroethyl, 1-trifluoro-methylethyl, methoxyethyl, 2-ethoxy-propyl and butoxyethyl fur-3-yl-glycolate; butyl 7-methoxybenzofur-3-yl-glycolate, propyl 6-methl- or 6-chlorobenzofur-3-yl glycolate, and ethyl and butyl benzofur-3-yl-glycolate.

The benzofur-3-ylglycolates of the general formula (VIa),

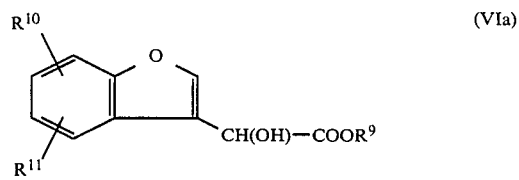

in which $R^9$, $R^{10}$ and $R^{11}$ have the above-mentioned meanings, and their precursors are still unknown.

They are obtained when glyoxylates are added photochemically to benzofuran or the substituted benzofurans in a solvent which is inert for photochemical reactions, and the resulting 2,7-dioxabicyclo[3.2.0]-hept-3-enes are isomerized using acid.

If, for example, ethyl glyoxylate and 7-methylbenzofuran are employed according to this method, the course of the reaction can be represented by the following equation:

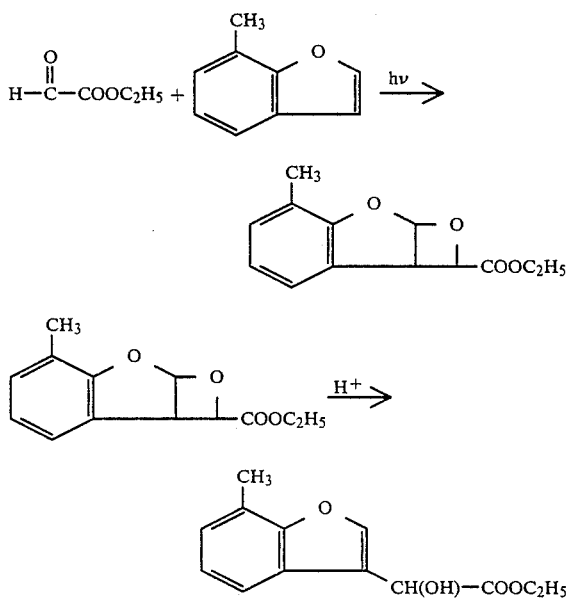

The photoadditions, are carried out under an inert atmosphere, such as, for example, nitrogen or a noble gas. Suitable diluents are all solvents which are inert for photochemical reactions. Benzene, toluene, dioxane, acetonitrile or 1,2-dimethoxyethane, for example, should be mentioned here.

The isomerizations of the 2,7-dioxabicyclo[3.2.0-]hept-3-enes are carried out at great dilution in inert organic solvents, for example diethyl ether, methlene chlorine or dioxane. Preferred solutions are those containing 0.001 to 1 mol of 2,7-dioxabicyclo-[3.2.0]hept-3-ene per liter of solvent. Protic acids, preferably p-toluenesulfonic acid, benzenesulfonic acid and methanesulfonic acid, are suitable as acid catalysts. Due to side reactions, it is uneconomic to process concentrated solutions.

Reagents which oxidize a secondary alcohol to a ketone (see J. March, Advanced Organic Chemistry, McGraw Hill Kogakusha Ltd. 1977, p. 1082), preferably chromium trioxide, lead tetraacetate and manganese dioxide, may be used as oxidant for the preparation of the fur-3-yl-glyoxylates from the fur-3-yl-glycolates. Suitable diluents are inert solvents such as benzene, toluene, acetic acid or methylene chloride, or alternatively pyridine and quinoline.

Suitable diluents for process (a) for the preparation of the compounds of the general formula(I) are all organic solvents which are inert towards the reactants; polar solvents are used preferably. Acetonitrile, acetone, chloroform, benzonitrile, dimethylacetamide, dimethylformamide, dimethyl sulphoxide, chlorobenzene, ethyl acetate, dioxane, methyl ethyl ketone, methylene chloride and tetrahydrofuran, for example, should be mentioned here.

Tert.-amines, such as triethylamine triethylenediamine, pyridine or 4-dimethyolaminopyridine, or alternatively lead naphthenate and dibutyltin dioxide may be used as catalysts for the reaction of the isocyanates with the hydroxythiophenes.

The reaction temperatures and the reaction duration are determined by the activity of the starting materials. In general, temperatures between 20° C. and 120° C., preferably between 60° C. and 100° C., are used.

It may be necessary to employ an excess of the isocyanate of the formula (II) in the reaction.

According to process (b), a mixture consisting of a 4-hydroxythiophene derivative of the formula (III), a tert.-amine, such as, for example, quinoline, dimethylbenzylamine, dimethylaniline, ethyldicyclohexylamine, ethyldiisopropylamine, picoline, pyridine or triethylamine, and an inert organic solvent, such as, for example, methylene chloride, chloroform, chlorobenzene, ethyl acetate, toluene or xylene, is added to excess phosgene, dissolved in the inert organic solvent, in a first stage. The temperature is, in general, between −50° C. and +80° C., preferably at 0° C. to +30° C.

After isolating the 3-chlorocarbonyloxythiophene derivative of the formula (IV), this is reacted with an amine of the formula (V) or with a salt of the amine of the formula (V), the resulting acid being bonded to a tert.-amine for economic reasons. If an amine salt is introduced into the reaction, twice the amount of the tert.-amine should be employed. In principle, water-miscible or non-miscible solvents, as listed above, are suitable for this reaction. In general, the reaction is carried out at temperatures corresponding to the phosgenation reaction.

Depending on the working conditions, the active compounds according to the invention precipitate out in crystalline form, or they remain dissolved in the organic solvent and may be precipitated, after washing the solution with water, by careful concentration of the solution or by addition of a little polar organic solvent, such as cyclohexane, dibutyl ether, diisopropyl ether or carbon tetrachloride. If appropriate, water-miscible polar solvents must be removed after the reaction by evaporation in vacuo.

If the compounds according to the invention are dissovled in a water-miscible solvent, they can alternatively be precipitated by addition of water.

In general, both processes are carried out at atmospheric pressure.

As acid components, the amine salts of the formula (V) may contain, for example, hydrochloric acid, hydrobromic acid and hydrofluoric acid, particularly hydrochloric acid, furthermore nitric acid, sulphuric acid, acetic acid, furmaric acid, methanesulphonic acids, benzenesulphonic acids or toluenesulphonic acids.

Some of the compounds according to the invention decompose at elevated temperature; in these cases, the melting points can only be determined with low accuracy or not at all. The presence of certain structural elements can be seen from the NMR spectra.

The active compounds according to the invention display a strong biological action and may be employed in practice for combating undesired pests. The active compounds are, inter alia, suitable for use as plant protection agents, above all as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Bacterial agents are employed in plant protection for combating Pseudomonadaceae, Rhizobiaceae, Enterobacteriaceae, Corynebacteriacea and Streptomycetaceae.

Some causative organisms of fungal and bacterial diseases which come under the generic names listed above may be mentioned as examples, but not by way of limitation:

Xanthomonas species, such as, for example, *Xanthomonas campestris* pv. oryzae; Pseudomonas species, such as, for example, *Pseudomonas syringae* pv. lachrymans; Erwinia species, such as, for example, *Erwinia amylovora;* Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera Leucotrichia;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, Such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularaia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae;* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The new active compounds exhibit a particularly good activity against pathogens of fungal infections in rice, and in addition they are highly active against Omyceten, pathogens of apple scab, and also show good action against cereal diseases, for example, when used appropriately and at the appropriate concentration.

The active compounds can be converted to the customary formulations, such as solutions, emulsions, suspensions, powders, foams, pastes granules, aerosols, very fine capsules in polymeric substances and in coating compositions for seed as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and-/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, stronglypolar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylarl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by eight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

Preparation Examples of 2,5-bis-(isopropoxycarbonyl)-3-methyl-4-[5-(butyloxycarbonyl)-pentylaminocarbonyloxy]-thiophene are obtained as a viscous material.

$^1$H-NMR 80 MHz CDCl$_3$ δ-values OCH 2H m 5.0–5.5 ppm; OCH$_2$ 2H t 4.13 ppm; N—CH$_2$ 2H m 3.1–3.5 ppm; hetar-CH$_3$ s 2.39 ppm.

The following compounds of the formula (I) are obtained in an analogous fashion:

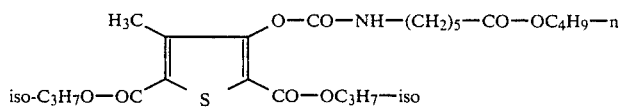

(I)

| Example No. | $R^1$ | $R^2$ | $R^3$ | Physical properties (M.p. = melting point) |
|---|---|---|---|---|
| 3 | —CH$_3$ | (CH$_3$)$_2$CH— | —(CH$_2$)$_5$—CN | M.p. 76° C. from diisopropyl ether |
| 4 | —CH$_3$ | (CH$_3$)$_2$CH— | —(CH$_2$)$_5$—COOC$_4$H$_9$—n | viscous material |
| 5 | —CH$_3$ | C$_6$H$_5$— | —(CH$_2$)$_5$—CN | viscous material |
| 6 | —C$_2$H$_5$ | H$_3$C— | —(CH$_2$)$_5$—CN | M.p. 90° C. from diisopropyl ether |
| 7 | —C$_3$H$_7$—n | H$_3$C— | —(CH$_2$)$_5$—CN | viscous |
| 8 | —CH(CH$_3$)$_2$ | H$_3$C— | —(CH$_2$)$_5$—CN | M.p. 72° C. from diisopropyl ether |
| 9 | —CH(CH$_3$)C$_2$H$_5$ | H$_3$C— | —(CH$_2$)$_5$—CN | viscous material |
| 10 | —CH$_2$C(CH$_3$)$_3$ | H$_3$C— | —(CH$_2$)$_5$—CN | viscous material |
| 11 | —CH(CH$_3$)$_2$ | H$_3$C— | —(CH$_2$)$_5$—COOC$_4$H$_9$—n | viscous material |
| 12 | —CH$_3$ | 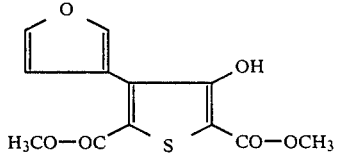 | —(CH$_2$)$_5$—CN | M.p. 97° C. from acetone/diisopropyl ether |
| 13 | —C$_2$H$_5$ | H$_3$C— | —C(CH$_3$)$_2$—CN | M.p. 108° C. from toluene/petroleum ether |
| 14 | —C$_4$H$_9$—n | H$_3$C— | —(CH$_2$)$_5$—CN | M.p. 61° from dibutyl ether |

EXAMPLE 1

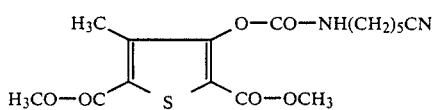

11.5 g of 2,5-bis-(methoxycarbonyl)-3-methyl-4-hydroxythiophene, 20 ml of anhydrous acetonitrile, 6.9 g of 5-cyanopentyl isocyanate and 20 mg of triethylene diamine are maintained at 78° C. for 4 hours. The acetonitrile is evaporated off in vacuo, and the evaporation residue is treated with diisopropyl ether. The crystals are separated off, washed with diisopropyl ether and dried at 60° C./0.1 mbar.

Yield: 15.6 g of 2,5-bis-(methoxycarbonyl)-3-methyl-4-(5-cyanopentylaminocarbonyloxy)-thiophene Melting point: 74° C.

EXAMPLE 2

10.0 g of 2,5-bis-(isopropoxycarbonyl)-3-methyl-4-hydroxythiophene, 20 ml of anhydrous acetonitrile, 15 g of butoxyarbonylpenthyl isocyanate (b.p. 149°–151°/13 millibar) and 100 mg of triethylene diamine are maintained at 100° C. for 18 hours. The mixture is diluted with 20 ml of acetonitrile. To remove the excess butoxycarbonylpentyl isocyanate, the reaction mixture is shaken three times with 50 ml of ligroin in each case. The acetonitrile phase is evaporated in vacuo. The evaporation residue is dried at 100° C./0.1 mbar. 16.3 g

EXAMPLE 14

(Precursor to the compound of Example 12) 2,5-bis-(methoxycarbonyl)-3-fur-3-yl-4-hydroxythiophene A mixture of 26 g of dimethyl thiodiacetate and 32 g of butyl 2-(fur-3-yl)-2-oxo-acetate is added dropwise, over 30 minutes at 64°–68° C., to a mixture of 100 ml of methyl alcohol and 39.9 g of potassium tert.-butanolate. The reaction mixture is kept at this temperature for a further 3 hours, and then poured into a mixture of 179 g of ice and 58 g of concentrated hydrochloric acid. The resultant crystals are separated off, washed with ice water until free of chloride, and dried at 60° C./0.1 mbar.

Yield: 27.9 g. The product is recrystallized from 250 ml of methyl alcohol, and 22 g of 2,5-bis-(methoxy-carbonyl)-3-fur-3-yl-4-hydroxythiophene having a melting point of 102° C. are obtained.

EXAMPLE 15

(Precursor to the compound of Example 14) Butyl 2-fur-3-yl)-2-oxo-acetate

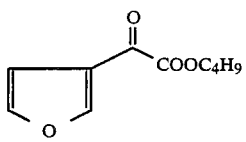

A mixture of 39.6 g of butyl fur-3-yl-glycolate and 88.6 g of lead tetraacetate in 400 ml of absolute benzene is refluxed for 8 hours. After cooling to room temperature, the salts are filtered off and washed with benzene and the combined benzene phases are shaken with a 10% strength sodium bicaronate solution and a saturated sodium chloride solution. After drying over sodium sulphate, filtering off and concentrating, the oily residue is distilled in vacuo. 32.7 g (83%) of an oil, boiling point 80° C. (0.3 Torr), $n_d^{20}=1.477$, are obtained.

$^1$H—NMR (80 MHz, CDCl$_3$, δ-values): 8.53 (s, 1H); 7.50 (t, 1H, J=1.5 Hz); 6.90 (d, 1H, J=1.5 Hz); 4.35 (t, 2H, J=7 Hz); 2.00−1.10 (m, 4H); 0.97 (t, 3H, J=7 Hz) IR (cap. film, v in cm$^{-1}$): 1772 1676 (C=O).

EXAMPLE 16

Butyl 2-(benzofur-3-yl)-2-oxo-acetate

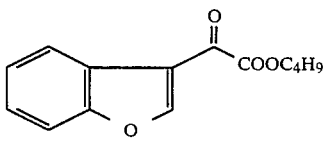

14.9 g of butyl benzofur-3-yl-glycolate and 26.6 g of lead tetraacetate are refluxed for 8 hours in 125 ml of absolute benzene. After working up as described in Example 15, 8.7 g (59% of theory) of an oil, boiling point 132°-136° C. (1 Torr), $n_D^{20}=1.537$, are obtained.

$^1$H—NMR (80 MHz, CDCl$_3$, δ-values): 8.88 (s, 1H); 8.28 (m, 1H); 7.43 (m, 3H); 4.38 (t, 2H, J=6.5 Hz); 2.00–1.45 (m, 4H); 0.98 (t, 3H, J=7 Hz).

EXAMPLE 17

(Precursor to the compound of Example 16) Butyl benzofur-3-yl-glycolate

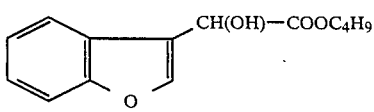

A solution of 0.7 g of p-toluenesulphonic acid in 340 ml of absolute ether is added dropwise to a solution of 49.6 g of 3,4-benzo-6-butoxycarbonyl-2,7-dioxabicyclo[3.2.0]hept-3-ene in 340 ml of absolute ether. After maintaining at room temperature for 48 hours, the mixture is neutralized using triethylamine, filtered, and concentrated. Vacuum distillation produces 25.3 g of butyl benzofur-3-yl-glycolate as an oil, boiling point 145°-150° C. (0.7 Torr), $n_D^{20}=1.5308$.

$^1$H—NMR (80 MHz, CDCl$_3$, δ-values): 7.85−7.10 (m, 5H); 7.70 (s, 1H); 5.41 (s, 1H); 4.18 (t, 2H, J=7 Hz); 3.66 (s, 1H); 1.80-0.98 (m, 4H); 0.98 (t, 3H, J=7 Hz).

IR (cap. film, v in cm$^{-1}$): 3475 (O—H), 1740 (C=O).

EXAMPLE 18

(Precursor to the compound of Example 17) 3,4-benzo-6-butoxycarbonyl-2,7-dioxabicyclo[3.2.0]hept-3-ene

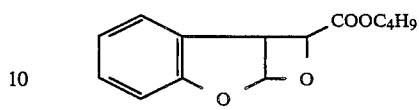

A solution of 26.0 g of butyl glyoxylate and 11.8 g of benzofuran in 150 ml of benzene is irradiated for 60 hours at room temperature under nitrogen. A Philips HPK 125 W high-pressure mercury lamp in a water-cooled pyrex glass sleeve is used as the irradiation source. After removing the volatile components by distillation, the product is isolated by distillation in a high vacuum. 5 g of 3,4-benzo-2,7-dioxabicyclo[3.2.0]-hept-3-ene as an oil, boiling point 140°-144° C. (0.4 Torr), $n_D^{20}=1.508$.

$^1$H—NMR (80 MHz, CDCl$_3$, δ-values): 7.45–6.80 (m, 4H); 6.63 (d, 1H, J=4.0 Hz); 4.87 (d, 1H, J=3.0 Hz), 4.33 (t, 1H, J=3.0 Hz); 4.28 (t, 2, J=7.0 Hz); 1.95–1.13 (m, 4H); 0.98 (t, 3H, J=7.0 Hz).

Use Example

Example A

Pyricularia test (rice)/protective

Solvent: 12.5 parts by weight of acetone

Emulsifier: 0.3 parts by weight of alkylaryl polyglycol ether

To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, for example, good activity is shown by the compounds according to preparation Examples 8, 1, 9, 7, 5 and 12.

It is understood that the specification and examples are illustrative but not limitative of the present invention and that other embodiments within the spirit and scope of the invention will suggest themselves to those skilled in the art.

I claim:

1. A hydroxythiophene derivative of the formula

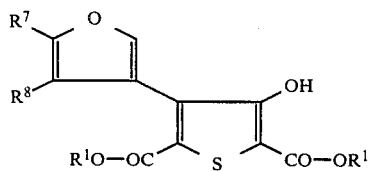

in which $R^1$ represents alkyl, alkoxyalkyl, alkylthioalkyl, fluoroalkyl, cyanoalkyl, alkenyl, alkynyl, or cycloalkyl,
$R^7$ and $R^8$ denote hydrogen or, together with the furyl radical to which they are bound, represent a benzofuryl radical of the formula
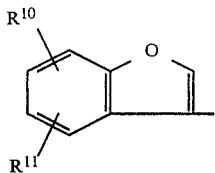
in which
$R^{10}$ and $R^{11}$, independently of one another, denote hydrogen, halogen, alkyl or alkoxy.
* * * * *